US006539310B2

(12) United States Patent
Shimomura

(10) Patent No.: US 6,539,310 B2
(45) Date of Patent: Mar. 25, 2003

(54) BODY TYPE DETERMINATION APPARATUS

(75) Inventor: Miyuki Shimomura, Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/983,388

(22) Filed: Oct. 24, 2001

(65) Prior Publication Data

US 2002/0049546 A1 Apr. 25, 2002

(30) Foreign Application Priority Data

Oct. 25, 2000 (JP) .................................. 2000-325249

(51) Int. Cl.$^7$ ........................... G01N 33/48; A61B 5/00
(52) U.S. Cl. ...................... 702/19; 600/300; 600/547
(58) Field of Search ..................... 702/19; 600/547, 600/300, 301; 128/903; 174/113 R, 108, 69

(56) References Cited

U.S. PATENT DOCUMENTS

| | | | | |
|---|---|---|---|---|
| 5,763,837 A | * | 6/1998 | Davignon et al. | 174/108 |
| 6,208,890 B1 | * | 3/2001 | Sarrazin et al. | 600/547 |
| 6,280,396 B1 | * | 8/2001 | Clark | 600/547 |
| 6,292,690 B1 | * | 9/2001 | Petrucelli et al. | 600/547 |
| 6,327,494 B1 | * | 12/2001 | Sakai | 600/547 |
| 6,353,755 B1 | * | 3/2002 | Oguma | 600/547 |
| 6,354,996 B1 | * | 3/2002 | Drinan et al. | 128/903 |
| 6,360,124 B1 | * | 3/2002 | Iwabuchi | 600/547 |
| 6,393,317 B1 | * | 5/2002 | Fukuda et al. | 600/372 |

FOREIGN PATENT DOCUMENTS

| | | |
|---|---|---|
| EP | 0545014 A | 6/1993 |
| EP | 0998875 A | 5/2000 |
| JP | 10-192258 | 7/1998 |
| WO | WO 96/08198 | 3/1996 |
| WO | WO 99/52425 | 10/1999 |

* cited by examiner

Primary Examiner—John S. Hilten
Assistant Examiner—Hien Vo
(74) Attorney, Agent, or Firm—McDermott, Will & Emery

(57) ABSTRACT

An object of the present invention is to provide an easy-understandable representation of fat tissue and lean tissue respectively occupying in a body constitution of a subject. Another object thereof is to help the subject determine which one of the fat tissue or the lean tissue is decreasing by weight reduction. A body type determination apparatus according to the present invention calculates an index of body fat mass, FMI (Fat Mass Index: fat mass/body height$^2$), an index of lean mass, LMI (Lean Mass Index: lean mass/body height$^2$), and a body build index, BMI (Body Mass Index: body weight/body height$^2$) from entered body data and a measured bioelectric impedance, and further the apparatus displays a relationship between the BMI and the FMI and/or between the BMI and the LMI as a result of measurement by way of a graph and/or an illustration.

10 Claims, 14 Drawing Sheets

FIG.4

|  | Under 30 yrs. | 30 yrs.and up | Obesity |
|---|---|---|---|
| Male | 14~20% | 17~23% | 25% and up |
| Female | 17~24% | 20~27% | 30% and up |

FIG. 5

Criteria on fat and lean for respective body types of a male aged under 30 years Fat criterion

| BMI | Extra low FMI range | Acceptable FMI range | Obese FMI range |
|---|---|---|---|
| 17 | Under 2.4 | 2.4~3.4 | 4.2~ |
| 18 | Under 2.5 | 2.5~3.6 | 4.5~ |
| 19 | Under 2.7 | 2.7~3.8 | 4.8~ |
| 20 | Under 2.8 | 2.8~4.0 | 5.0~ |
| 21 | Under 2.9 | 2.9~4.2 | 5.2~ |
| 22 | Under 3.1 | 3.1~4.4 | 5.5~ |
| 23 | Under 3.2 | 3.2~4.6 | 5.7~ |
| 24 | Under 3.4 | 3.4~4.8 | 6.0~ |
| 25 | Under 3.5 | 3.5~5.0 | 6.3~ |
| 26 | Under 3.6 | 3.6~5.2 | 6.5~ |
| 27 | Under 3.8 | 3.8~5.4 | 6.8~ |
| 28 | Under 3.9 | 3.9~5.6 | 7.0~ |
| 29 | Under 4.1 | 4.1~5.8 | 7.3~ |
| 30 | Under 4.2 | 4.2~6.0 | 7.5~ |

Lean criterion

| BMI | Extra low LMI range | Acceptable LMI range | Athlete type LMI range |
|---|---|---|---|
| 17 | Not greater than 12.7 | 13.6~14.6 |  |
| 18 | Not greater than 13.5 | 14.4~15.5 |  |
| 19 | Not greater than 14.3 | 15.2~16.4 |  |
| 20 | Not greater than 15.0 | 16.0~17.2 |  |
| 21 | Not greater than 15.7 | 16.8~18.1 |  |
| 22 | Not greater than 16.5 | 17.6~18.9 | Greater than the acceptable range |
| 23 | Not greater than 17.2 | 18.4~19.8 |  |
| 24 | Not greater than 18.0 | 19.2~20.6 |  |
| 25 | Not greater than 18.8 | 20.0~21.5 |  |
| 26 | Not greater than 19.5 | 20.8~22.4 |  |
| 27 | Not greater than 20.3 | 21.6~23.3 |  |
| 28 | Not greater than 21.0 | 22.4~24.1 |  |
| 29 | Not greater than 21.8 | 23.2~24.9 |  |
| 30 | Not greater than 22.5 | 24.0~25.8 |  |

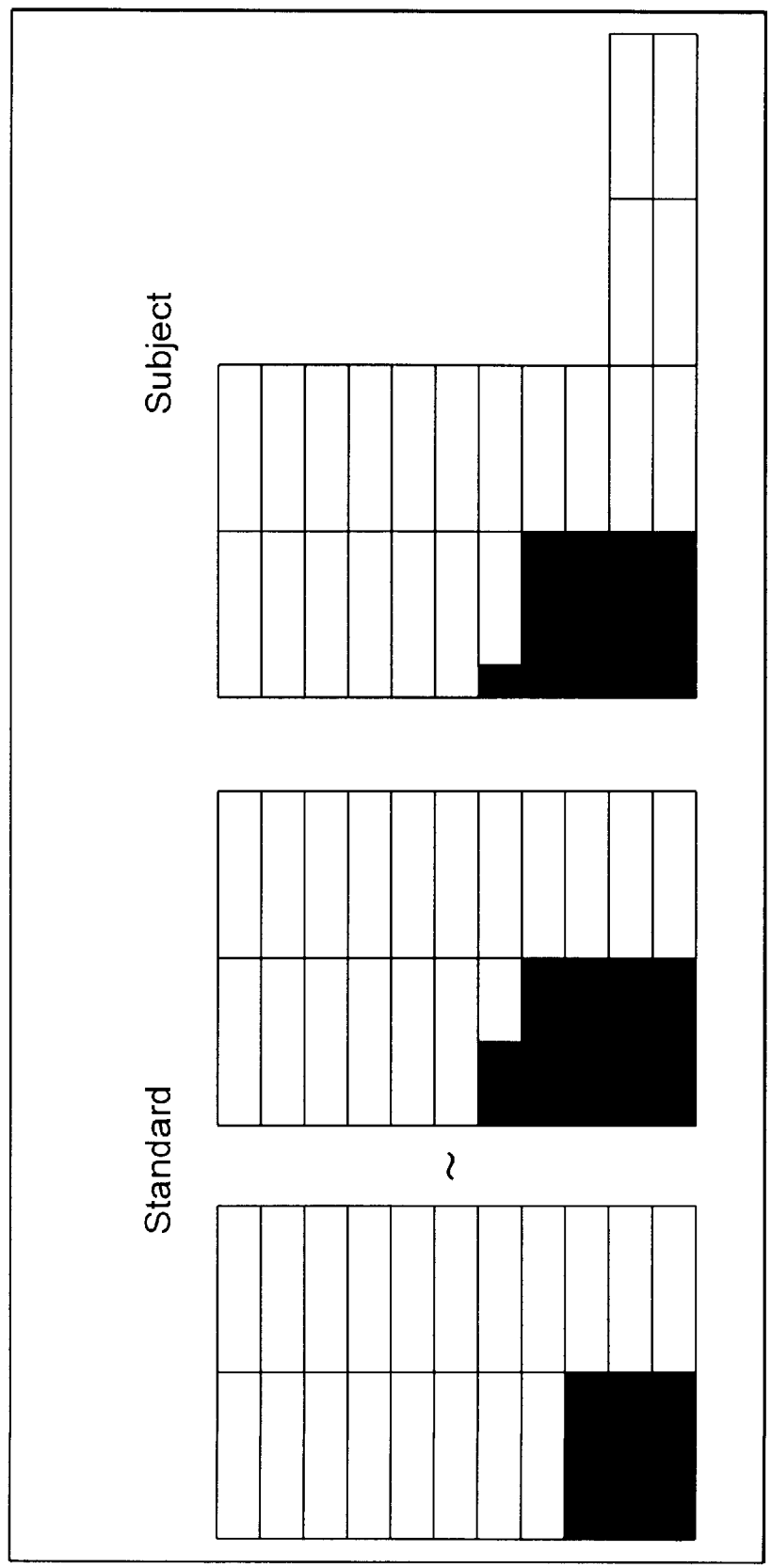

FIG. 12A

Index and advisory message for a male aged under 30

| BMI | FMI | LMI | Advisory indication |
|---|---|---|---|
| 17 | Under 2.4<br>2.4~3.4<br>3.5~4.1<br>4.2~ | 14.7~<br>13.6~14.6<br>12.9~13.5<br>not more than 12.7 | Low in weight and fat but high in lean. Athlete type.<br>Low in weight but standard in fat and lean.<br>Low in weight but a bit high in fat with a bit low in lean.<br>Low in weight but high in fat with low in lean. |
| 18 | Under 2.5<br>2.5~3.6<br>3.7~4.4<br>4.5~ | 15.6~<br>14.4~15.5<br>13.6~14.3<br>not more than 13.5 | Low in weight and fat but high in lean. Athlete type.<br>Low in weight but standard in fat and lean.<br>Low in weight but a bit high in fat with a bit low in lean.<br>Low in weight but high in fat with low in lean. |
| 19 | Under 2.7<br>2.7~3.8<br>3.9~4.7<br>4.8~ | 16.5~<br>15.2~16.4<br>14.2~15.1<br>not more than 14.3 | Acceptable weight, low in fat and high in lean.<br>Standard in weight, fat and lean.<br>Acceptable weight, a bit high in fat and a bit low in lean.<br>Acceptable weight, high in fat and low in lean. |
| 20 | Under 2.8<br>2.8~4.0<br>4.1~4.9<br>5.0~ | 17.3~<br>16.0~17.2<br>14.9~15.9<br>not more than 15.0 | Acceptable weight, low in fat and high in lean.<br>Standard in weight, fat and lean.<br>Acceptable weight, a bit high in fat and a bit low in lean.<br>Acceptable weight, high in fat and low in lean. |
| 21 | Under 2.9<br>2.9~4.2<br>4.3~5.1<br>5.2~ | 18.2~<br>16.8~18.1<br>15.6~16.7<br>not more than 15.7 | Acceptable weight, low in fat and high in lean.<br>Standard in weight, fat and lean.<br>Acceptable weight, a bit high in fat and a bit low in lean.<br>Acceptable weight, high in fat and low in lean. |
| 22 | Under 3.1<br>3.1~4.4<br>4.5~5.4<br>5.5~ | 19.0~<br>17.6~18.9<br>16.4~17.5<br>not more than 16.5 | Acceptable weight, low in fat and high in lean.<br>Standard in weight, fat and lean.<br>Acceptable weight, a bit high in fat and a bit low in lean.<br>Acceptable weight, high in fat and low in lean. |
| 23 | Under 3.2<br>3.2~4.6<br>4.7~5.6<br>5.7~ | 19.9~<br>18.4~19.8<br>17.1~18.3<br>not more than 17.2 | Acceptable weight, low in fat and high in lean.<br>Standard in weight, fat and lean.<br>Acceptable weight, a bit high in fat and a bit low in lean.<br>Acceptable weight, high in fat and low in lean. |

FIG. 12B

Index and advisory message for a male aged under 30

| BMI | FMI | LMI | Advisory indication |
|---|---|---|---|
| 24 | Under 3.4<br>3.4~4.8<br>4.9~5.9<br>6.0~ | 20.7~<br>19.2~20.6<br>17.9~19.1<br>not more than 18.0 | Acceptable weight, low in fat and high in lean.<br>Standard in weight, fat and lean.<br>Acceptable weight, a bit high in fat and a bit low in lean.<br>Acceptable weight, high in fat and low in lean. |
| 25 | Under 3.5<br>3.5~5.0<br>5.1~6.2<br>6.3~ | 21.6~<br>20.0~21.5<br>18.7~19.9<br>not more than 18.8 | High in weight, low in fat and high in lean. Athlete type.<br>High in weight, but standard in fat and lean.<br>High in weight, and a bit high in fat and a bit low in lean.<br>High in weight and fat, but low in lean. |
| 26 | Under 3.6<br>3.6~5.2<br>5.3~6.4<br>6.5~ | 22.5~<br>20.8~22.4<br>20.7~19.4<br>not more than 19.5 | High in weight, low in fat and high in lean. Athlete type.<br>High in weight, but standard in fat and lean.<br>High in weight, and a bit high in fat and a bit low in lean.<br>High in weight and fat, but low in lean. |
| 27 | Under 3.8<br>3.8~5.4<br>5.5~6.7<br>6.8~ | 23.4~<br>21.6~23.3<br>20.2~21.5<br>not more than 20.3 | High in weight, low in fat and high in lean. Athlete type.<br>High in weight, but standard in fat and lean.<br>High in weight, and a bit high in fat and a bit low in lean.<br>High in weight and fat, but low in lean. |
| 28 | Under 3.9<br>3.9~5.6<br>5.7~6.9<br>7.0~ | 24.2~<br>22.4~24.1<br>20.9~22.3<br>not more than 21.0 | High in weight, low in fat and high in lean. Athlete type.<br>High in weight, but standard in fat and lean.<br>High in weight, and a bit high in fat and a bit low in lean.<br>High in weight and fat, but low in lean. |
| 29 | Under 4.1<br>4.1~5.8<br>5.9~7.2<br>7.3~ | 25.0~<br>23.2~24.9<br>21.7~23.1<br>not more than 21.8 | High in weight, low in fat and high in lean. Athlete type.<br>High in weight, but standard in fat and lean.<br>High in weight, and a bit high in fat and a bit low in lean.<br>High in weight and fat, but low in lean. |
| 30 | Under 4.2<br>4.2~6.0<br>6.1~7.4<br>7.5~ | 25.9~<br>24.0~25.8<br>22.4~23.9<br>not more than 22.5 | High in weight, low in fat and high in lean. Athlete type.<br>High in weight, but standard in fat and lean.<br>High in weight, and a bit high in fat and a bit low in lean.<br>High in weight and fat, but low in lean. |

BODY TYPE DETERMINATION APPARATUS

BACKGROUND OF THE INVENTION

1. Field of the Invention

The present invention relates to an apparatus for measuring a body fat mass and a lean mass based on the bioelectric impedance method, and in particular, to a display mode for said apparatus.

2. Prior Art

There has been used an arithmetic method for determining whether or not a subject is obese, in which a BMI (Body Mass Index) is calculated to determine a ratio of a body weight of the subject to a reference body weight. The BMI is expressed by the following equation:

$$BMI = M/L^2$$

where, a body height is L(m) and a body weight is M(kg).

The BMI is an index used to indicate a body build of the subject and therefore useful.

Generally, regardless of the sex and age of the subject, a body type with the BMI within a range of 18.5 to 25 is considered as standard, with a value below said range as skinny, with a value exceeding said range as obese, and with the BMI of 22 as ideal. However, with that index only, it is impossible to see a physical constitution of a body.

Accordingly, a body fat meter for measuring a ratio of body fat occupancy in a body based on the bioelectric impedance method has been commonly used, in which a body fat rate is indicated by a numeric figure or a transition of the body fat rate is represented by a graph.

Among those body fat meters, a body fat meter disclosed in the Japan Patent Application Laid-open No. H-10-192258 has taught that a BMI and a body fat rate are calculated and a relationship between them is indicated in the form of matrix.

By the way, it has been said that consumed energy affects an amount of basal metabolism, and it is an actual fact that the amount of basal metabolism being more or less does critically affect the accumulation of body fat. It has been considered that the energy consumption by fat tissue is extremely low while the energy consumption by muscular tissue is different depending on the tissue mass, wherein a body with more muscular tissues consumes more energy. It has been known that the volume of the lean tissue consisting mostly of the muscular tissue exhibits a proportional relationship with respect to the amount of the basal metabolism. Therefore, such a constitution consisting of more lean tissues should never be considered as being unhealthy but should be favorable for health.

However, with recent boom of encouraging diet, even a person of athlete type having the physical constitution of muscles rather than fat has been obsessed with an idea that he/she must be obese and forced himself/herself to reduce his/her weight.

Those prior-art body fat meters exhibits whether the ratio of body fat occupancy in the constitution of the body is large or not.

In addition, the body fat meter disclosed in the Japan Patent Application Laid-open No. H-10-192258 allows only the relationship between the body build and the body fat to be grasped.

Further, despite of the fact that lean tissue is important for the health from the viewpoint that the basal metabolism and consumed energy can be grasped therefrom, conventionally the body fat mass has been exclusively discussed, while no much attention has been paid on the lean tissue and the lean mass has never been indicated.

The present invention has been made in the light of the above problems, and an object thereof is to calculate and indicate the ratios of the body fat tissue and the lean tissue respectively occupying in a body constitution, and thus to facilitate a comprehensive evaluation of the body to be easily understandable. Another object of the present invention is, based on the above ratios, to facilitate an easier determination of which one of the fat tissue or the lean tissue decreasing by the weight reduction.

SUMMARY OF THE INVENTION

According to an aspect of the present invention, there is provided a body type determination apparatus comprising: an input device for entering personal body data; an impedance measuring device for measuring a bioelectric impedance; an arithmetic device for calculating an FMI and a BMI based on said entered body data and measured bioelectric impedance value; and a display device for providing a graphic representation of the calculated FMI and BMI.

Further, according to another aspect of the present invention, there is provided a body type determination apparatus comprising: an input device for entering personal body data; an impedance measuring device for measuring a bioelectric impedance; an arithmetic device for calculating an LMI and a BMI based on said entered body data and measured bioelectric impedance value; and a display device for providing a graphic representation of the calculated LMI and BMI.

Still further, according to another aspect of the present invention, there is provided a body type determination apparatus comprising: an input device for entering personal body data; an impedance measuring device for measuring a bioelectric impedance; an arithmetic device for calculating an FMI, an LMI and a BMI based on said entered body data and measured bioelectric impedance value; and a display device for providing a graphic representation of a relationship between the calculated FMI and BMI together with a relationship between the calculated LMI and BMI, all at once.

Yet further, according to another aspect of the present invention, there is provided a body type determination apparatus comprising: an input device for entering personal body data; an impedance measuring device for measuring a bioelectric impedance; an arithmetic device for calculating an FMI, an LMI and a BMI based on said entered body data and measured bioelectric impedance value; and a display device for providing a representation of the calculated BMI by using blocks, wherein said representation by blocks is displayed distinctively in different colors based on the calculated FMI and LMI.

Still further, a body type determination apparatus according to the present invention further comprises a body weight measuring device for measuring a body weight, wherein said arithmetic device uses the measured body weight value to calculate the BMI.

Yet further, a body type determination apparatus according to the present invention further comprises a body height measuring device, wherein said arithmetic device uses the measured body height to calculate the FMI and the BMI.

Still further, a body type determination apparatus according to the present invention further comprises a body height measuring device, wherein said arithmetic device uses the measured body height to calculate the LMI and the BMI.

BRIEF DESCRIPTION OF THE DRAWINGS

FIG. 4 is a table showing an acceptable range and a range considered as being obese for a body fat rate;

FIG. 5 shows tables of criteria for FMIs and LMIs in respective BMI values;

FIG. 11 is another example of indication in the body type determination apparatus of an embodiment according to the present invention;

FIGS. 12A and 12B are tables of advisory messages provided in a body type determination apparatus of an embodiment according to the present invention.

DESCRIPTION OF PREFERRED EMBODIMENTS

A body type determination apparatus according to the present invention calculates from entered body data and a measured bioelectric impedance (hereafter referred to as BI) an index of body fat mass, FMI (Fat Mass Index: fat mass/body height$^2$), an index of lean mass, LMI (Lean Mass Index: lean mass/body height$^2$), and a body build index, BMI (Body Mass Index: body weight/body height$^2$), and further the apparatus displays a relationship between the BMI and the FMI and/or between the BMI and the LMI as a result of measurement by way of a graph and/or illustration.

The term "body type" herein also covers a constitution related to a ratio between the fat mass and the lean mass in addition to its inherent meaning of "body type", and thus the body type determination apparatus of the present invention determines such constitution, as well as the body type.

An embodiment of the present invention will now be described with reference to the attached drawings.

Figure 1:
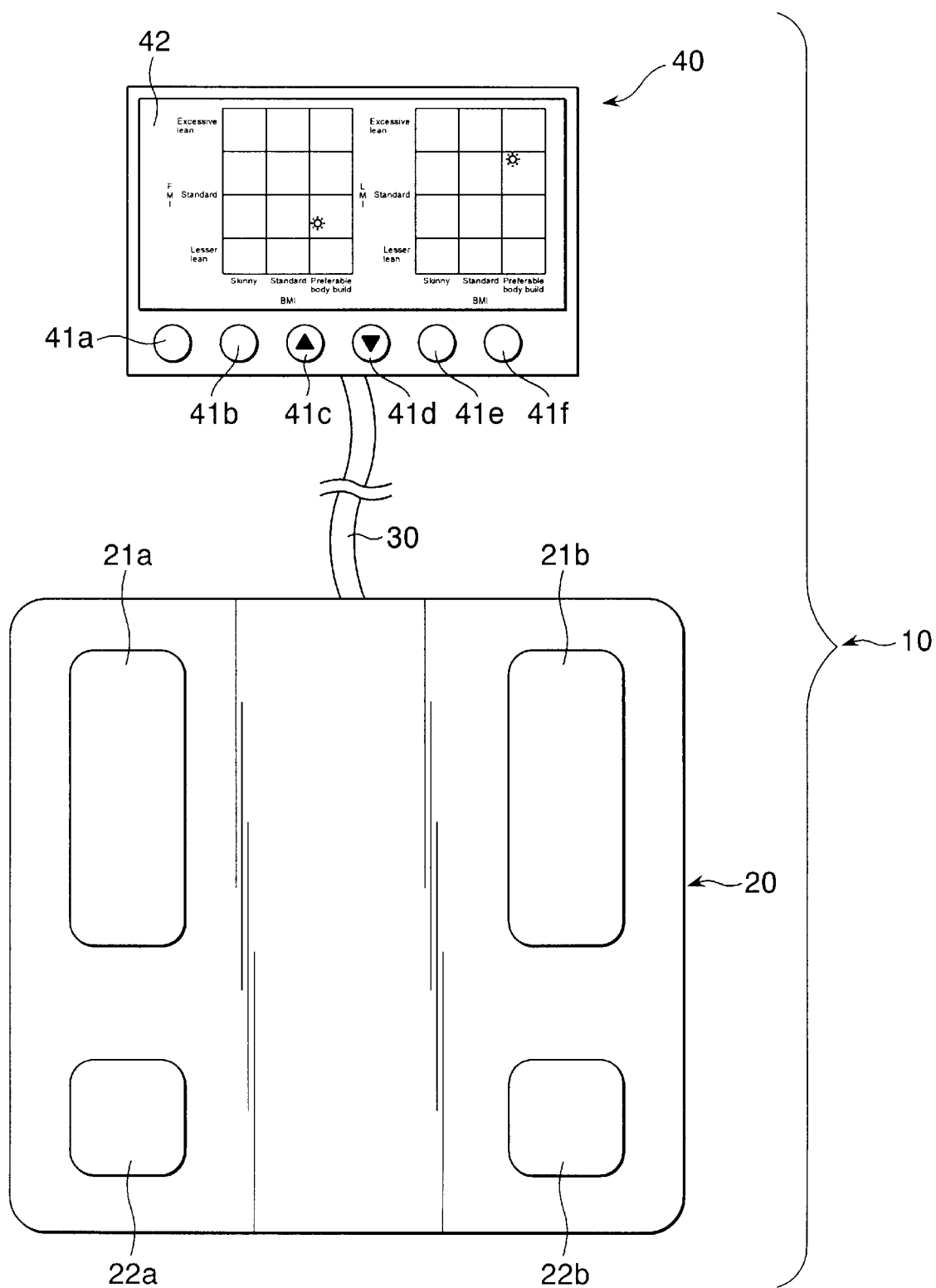
FIG. 1 is a front elevational view illustrating an external structure of a body type determination apparatus of an embodiment according to the present invention.

FIG. 1 is a front elevational view of a body type determination apparatus of one embodiment according to the present invention. As shown in FIG. 1, a body type determination apparatus 10 comprises a bioelectric impedance meter 20 equipped with a weight scale and a control box 40 connected to said bioelectric impedance meter 20 equipped with the weight scale via a electric cable 30. Although in this embodiment, the bioelectric impedance meter 20 equipped with the weight scale and the control box 40 have been connected to each other via the ordinary electric cable 30, they may be interconnected via, for example, a radio communication by way of infrared ray or electromagnetic wave.

In the top surface of the bioelectric impedance meter 20 equipped with the weight scale, electrodes for applying a constant current 21a and 21b and electrodes for measuring a voltage 22a and 22b are arranged, and further in the front face of the control box 40, a group of operation keys consisting of a power switch 41a, a measurement key 41b, an up key 41c, a down key 41d, a set key 41e and a graph key 41f and a display device 42 are arranged.

Figure 2:
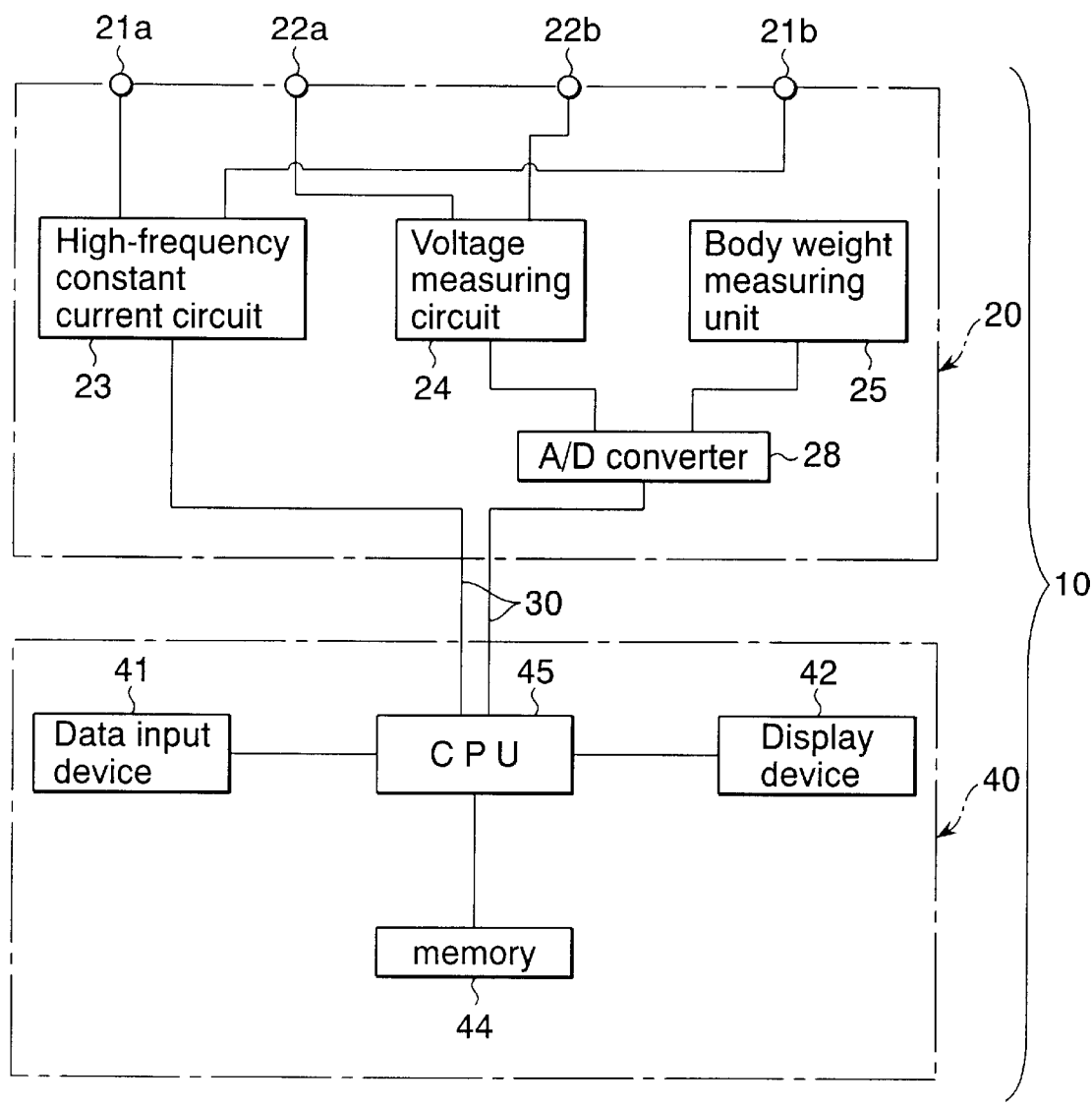
FIG. 2 is a block diagram of a functional structure of the body type determination apparatus shown in FIG. 1.

FIG. 2 is a block diagram illustrating a functional structure of the body type determination apparatus 10 shown in FIG. 1. As shown in FIG. 2, the bioelectric impedance meter 20 equipped with the weight scale comprises: the constant current feeding electrodes 21a and 21b; a high-frequency constant current circuit 23 for generating a high-frequency constant low current to be applied to said constant current feeding electrodes 21a and 21b; the voltage measuring electrodes 22a and 22b; a voltage measuring circuit 24 functioning as an impedance measurement device for measuring a voltage between said voltage measuring electrodes 22a and 22b; a body weight measuring unit 25 functioning as a body weight measurement device for measuring a body weight of a subject; and an A/D converter 28 for A/D converting a measured voltage and body weight.

Further, the control box 40 comprises: a data input device 41 functioning as an input device including the group of operation keys 41a to 41f for instructing a start of measurement and for entering data; a display device 42 functioning as a display device for providing a graphic representation of a determined body type and/or a determined result; a memory 44 functioning as a storage device for storing a measured BI and/or a calculated BMI, FMI, LMI and so on; and a CPU 45 functioning as both of an operation control device and a body-type determination device for determining a body type or the like based on the data entered by the input device 41, the measured BI and other data such as the body weight, and for controlling a storing operation of a variety of data into the memory 44 and/or an indication of the variety of data onto the display device 42.

Although in the present embodiment, respective functional elements have been separately disposed either in the bioelectric impedance meter 20 equipped with the weight scale or in the control box 40 as described above, the application of the present invention is not limited to this, but for example, the CPU 45 may be housed in the bioelectric impedance meter 20 equipped with the weight scale instead of the control box 40, or the bioelectric impedance meter 20 equipped with the weight scale may be integrated with the control box 40 to make up a single unit.

An operation of an embodiment of the body type determination apparatus described above will now be described.

Figure 3:
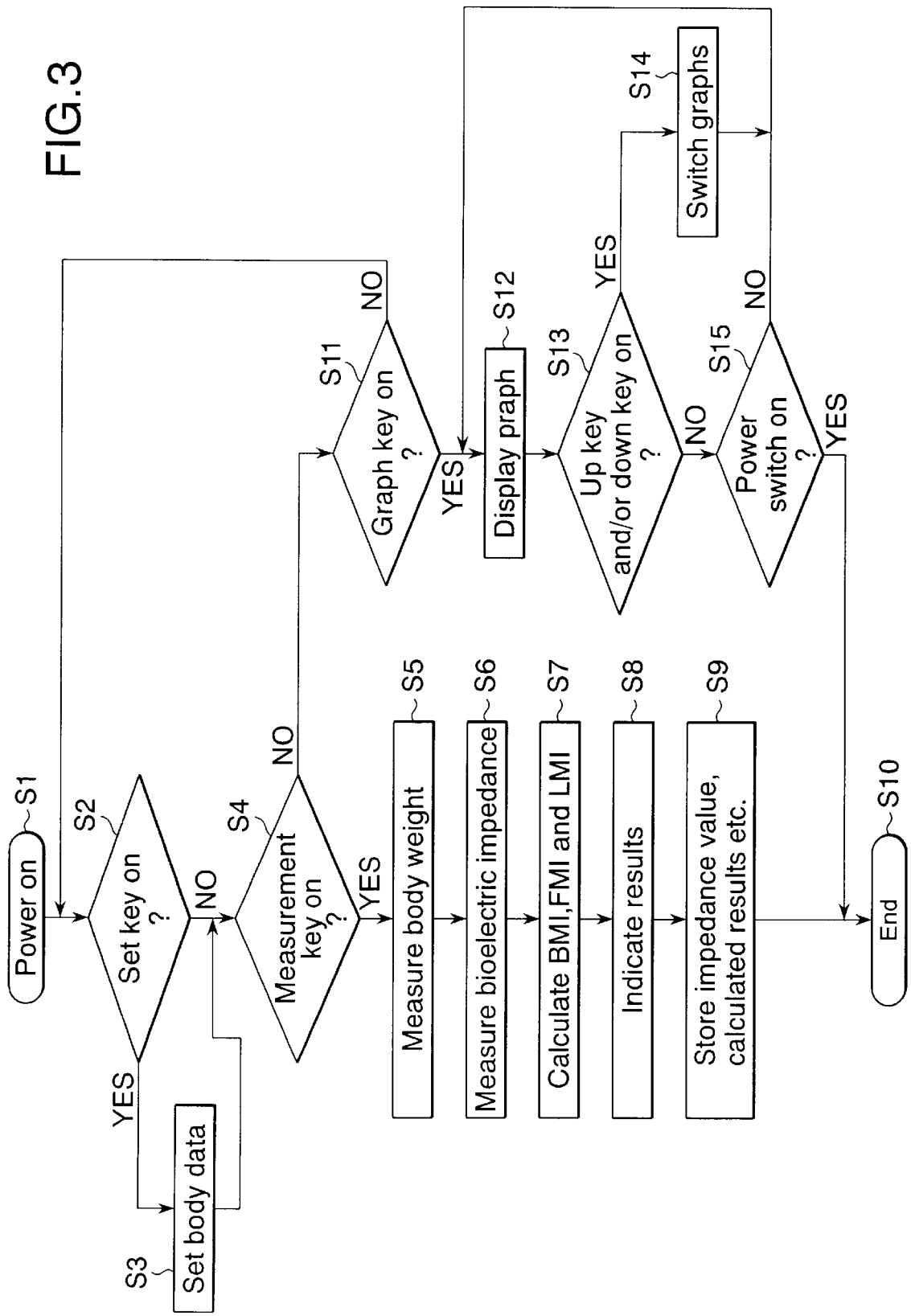
FIG. 3 is a flow chart illustrating a procedure in the body type determination apparatus of an embodiment according to the present invention.

FIG. 3 is a flow chart illustrating a procedure for determining a body type according to the present invention. At step 1, a subject depresses the power switch 41a to turn on the body type determination apparatus 10.

At step 2, if the subject depresses the set key 41e, then the body type determination apparatus 10 is turned in a setting mode and the process moves to step 3.

The step 3 is for setting the body data of the subject. The up key 41c and the down key 41d are used to change letters or figures displayed in the display device 42a until his/her body height, sex or age may be indicated. Those values which have been changed are sequentially determined by epressing the set key 41f again.

At step 4, if the subject depresses the measurement key 41b, then the body type determination apparatus is turned into a measuring mode and the process moves to step 5, but if the key 41b is not depressed, then the process moves to step 11 to determine whether the apparatus should be moved into a graphic representation mode or not.

The measuring mode starts at step 5. The subject stands on his/her bare feet on the bioelectric impedance meter 20 equipped with the weight scale such that his/her toes of the left and the right soles come in contact with the constant current feeding electrodes 21a and 21b respectively and his/her heels of the left and the right soles come in contact with the voltage measuring electrodes 22a and 22b respectively, and then the body weight measurement unit 25 detects the weight and starts to measure the body weight of the subject. Subsequently, at step 6, a high-frequency constant low current generated by the high-frequency constant current circuit 23 is applied to the toes of the subject through the constant current feeding electrodes 21a and 21b so as to flow between the legs including the lower abdominal region of the subject. Then, the voltage measuring circuit 24 measures a voltage appearing between the voltage measuring electrodes 22a and 22b and thus to measure a BI.

At step 7, the BMI, FMI and LMI are calculated based on the measured body weight, BI and set body height. Herein, a manner to determine the body type will be explained.

Those graphs used for the evaluation will be generated in the following manner.

(1) Assuming the BMI in a range of 17 to 31, a body height and a weight are established for each of the BMI values.

(2) To make an index, a body fat mass is determined from a body fat rate considered as a standard in order to determine a standard FMI. The acceptable range and the obese range in the table of FIG. 4 may be used to determine the standard body fat mass.

Herein, a specific case to make the index for a male (aged under 30) having the BMI of 17 will be explained.

Assume the body height of 171 cm, the body weight of 49.7 (it is to be noted that any combination of height and weight may be applicable so far as the resultant BMI is 17).

Calculating the acceptable FMI and the FMI for obesity, the resultant body fat mass for each cases are as follows:

$X/49.7 \times 100 = 14\%$ $X=7.0$ (minimum acceptable fat mass)

$X/49.7 \times 100 = 20\%$ $X=9.9$ (maximum acceptable fat mass)

$X/49.7 \times 100 = 25\%$ $X=12.4$ (obesity standard fat mass)

(3) Then, the FMI is calculated from the body fat mass/height$^2$.

The resultant values are:

$7.0/1.7^2=2.4$ (minimum acceptable FMI)

$9.9/1.7^2=3.4$ (maximum acceptable FMI)

$12.4/1.7^2=4.2$ (obesity standard FMI)

Based on the above calculations, it can be said for the person with the BMI of 17 that the acceptable FMI is in a range of 2.4 to 3.4, and the FMI of 4,2 or greater indicates the obesity. In this way, the standard values for FMI may be made respectively depending on the different BMIs (FIG. 5).

(4) At the point of time when the fat mass has been calculated, the equation: (body weight)−(body fat mass)= (lean mass) is used to determine the lean mass, from which the LMI is determined by the equation: LMI=lean mass/height$^2$. Otherwise, the LMI may be calculated by the equation: BMI−FMI=LMI.

Those tables shown in FIG. 5 are generated based on the resultant FMIs and LMIs.

Figure 6:
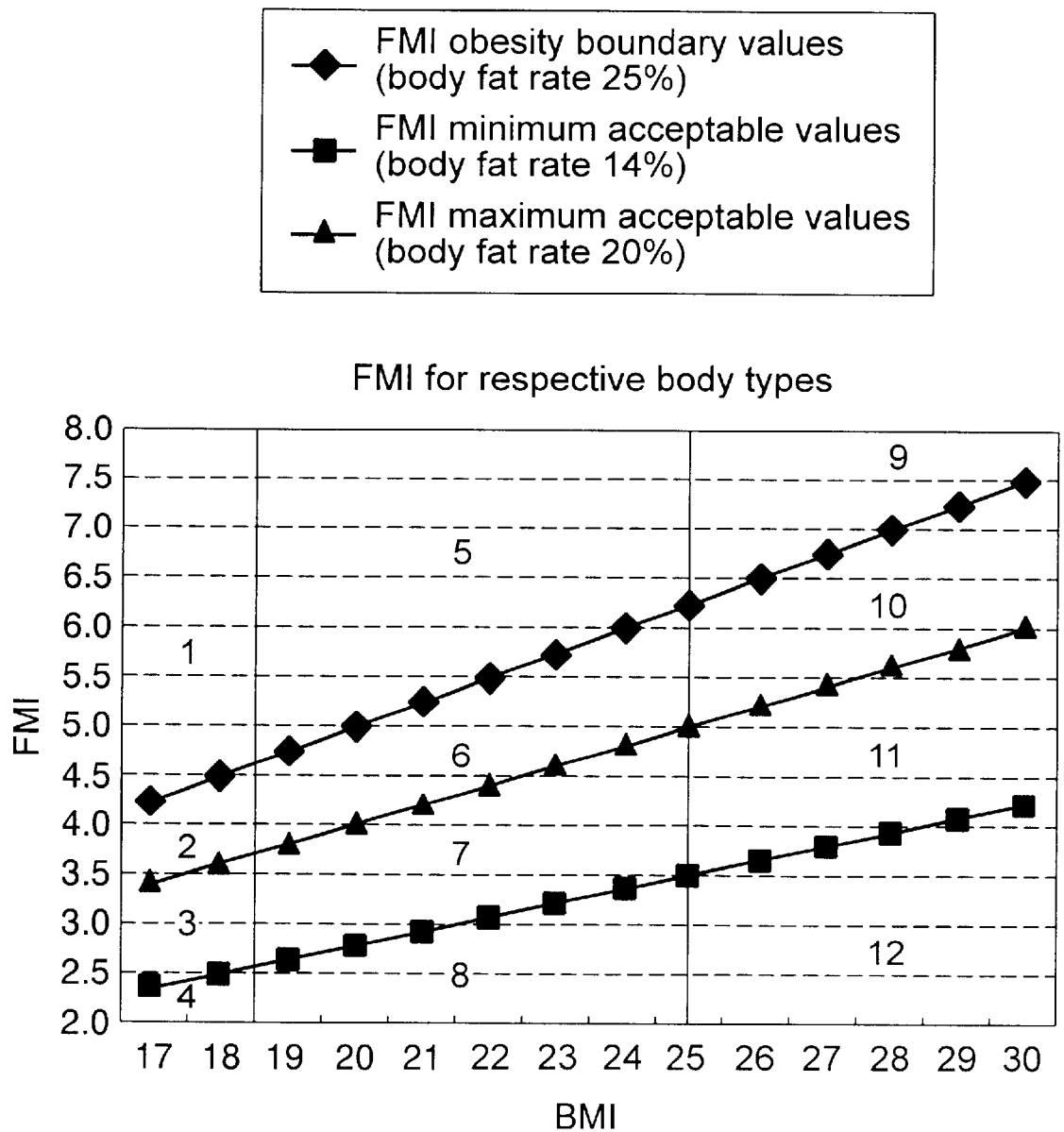
FIG. 6 is a chart showing reference lines for making a determination on the BMI and the FMI.
Figure 7:
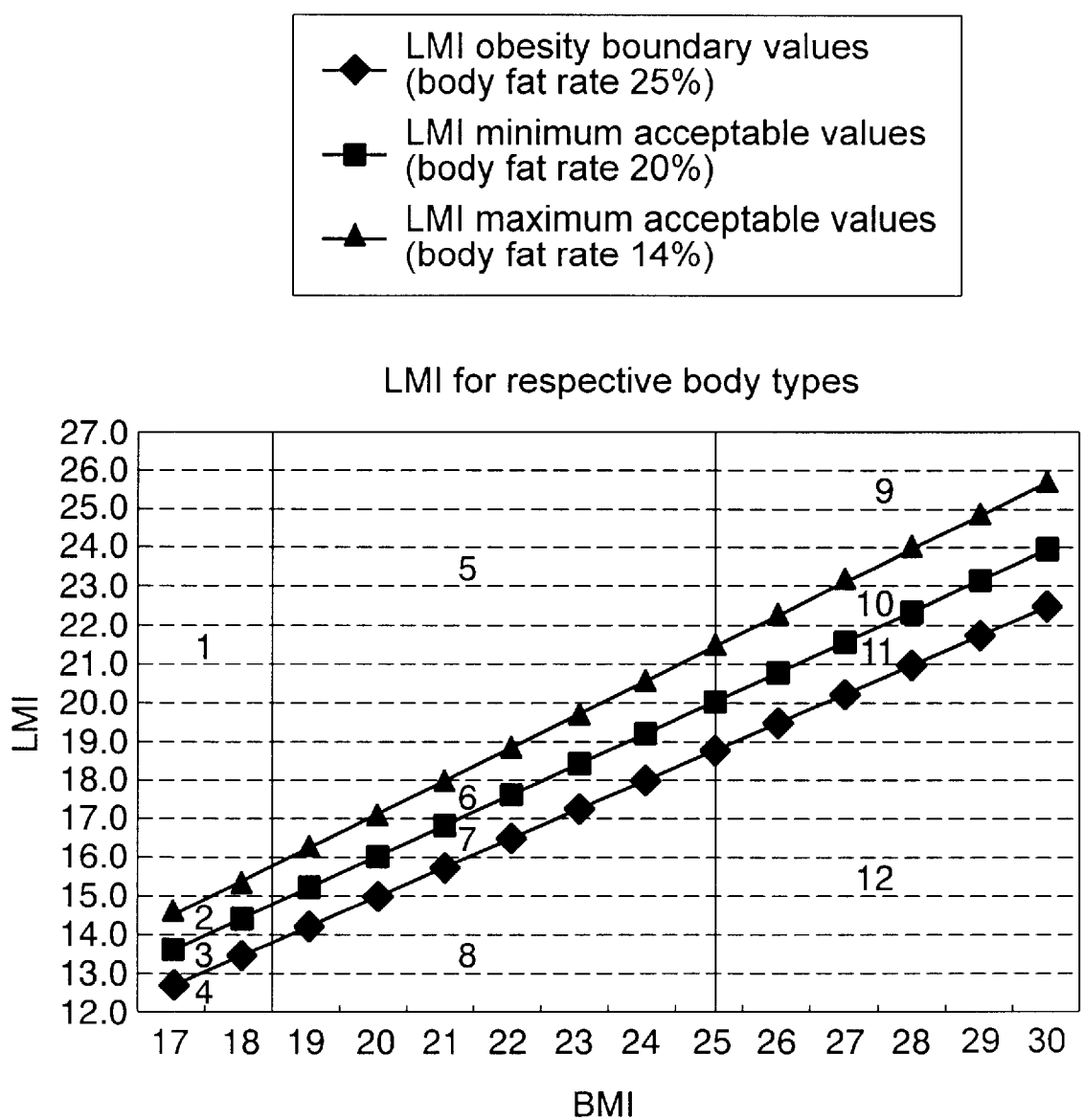
FIG. 7 is a chart showing reference lines for making a determination on the BMI and the LMI.

Those charts shown in FIGS. 6 and 7 are made based on FIG. 5.

Those acceptable values and obese values determined from the table 1 are plotted in a graph, in which the BMI is represented along the X-axis while the FMI along the Y-axis. This graph can be used as a criterion for the body fat (FIG. 6).

Likewise, those acceptable values and obese values determined from the table 1 are plotted in another graph, in which the BMI is represented along the X-axis while the LMI along the Y-axis. This graph can be used as a criterion for the muscle (FIG. 7).

Figure 8:
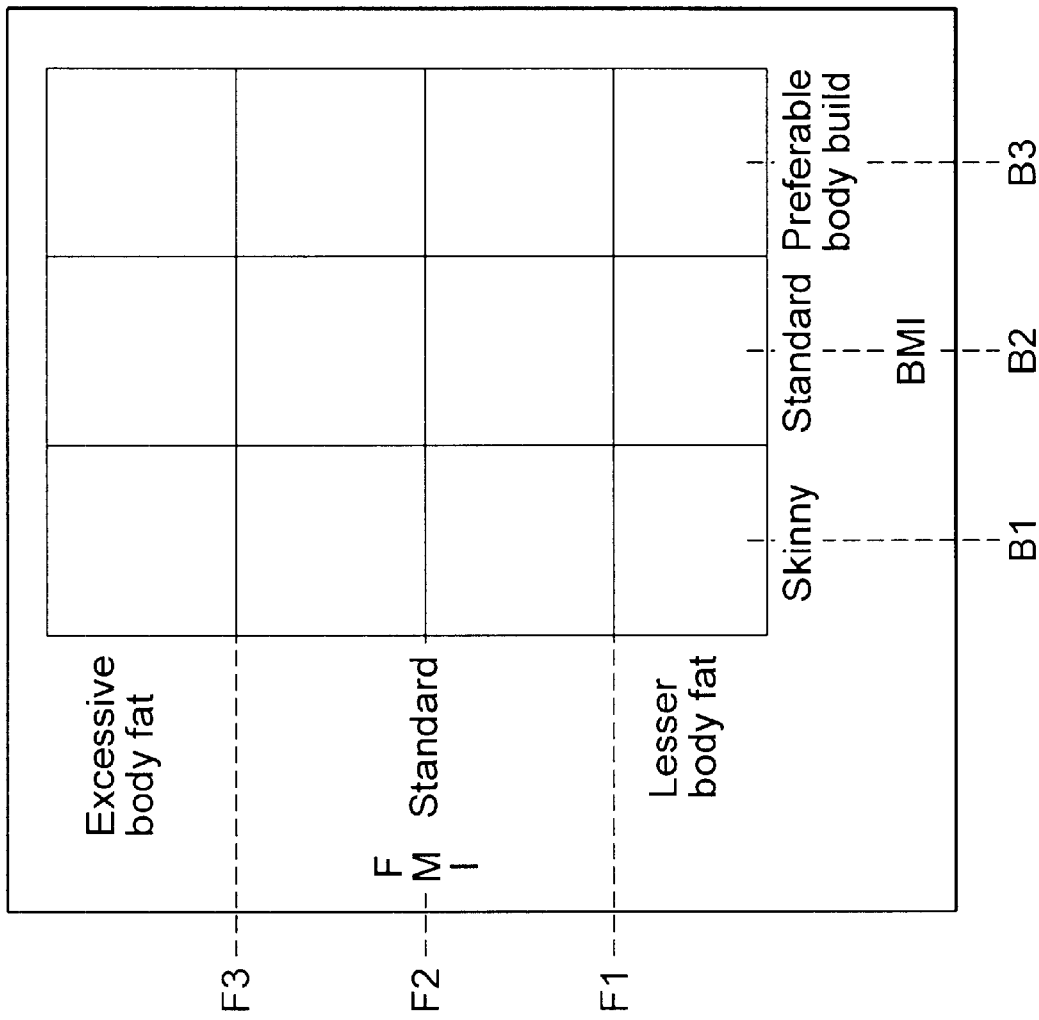
FIG. 8 is a chart illustrating a relationship between the BMI and the FMI.
Figure 9:
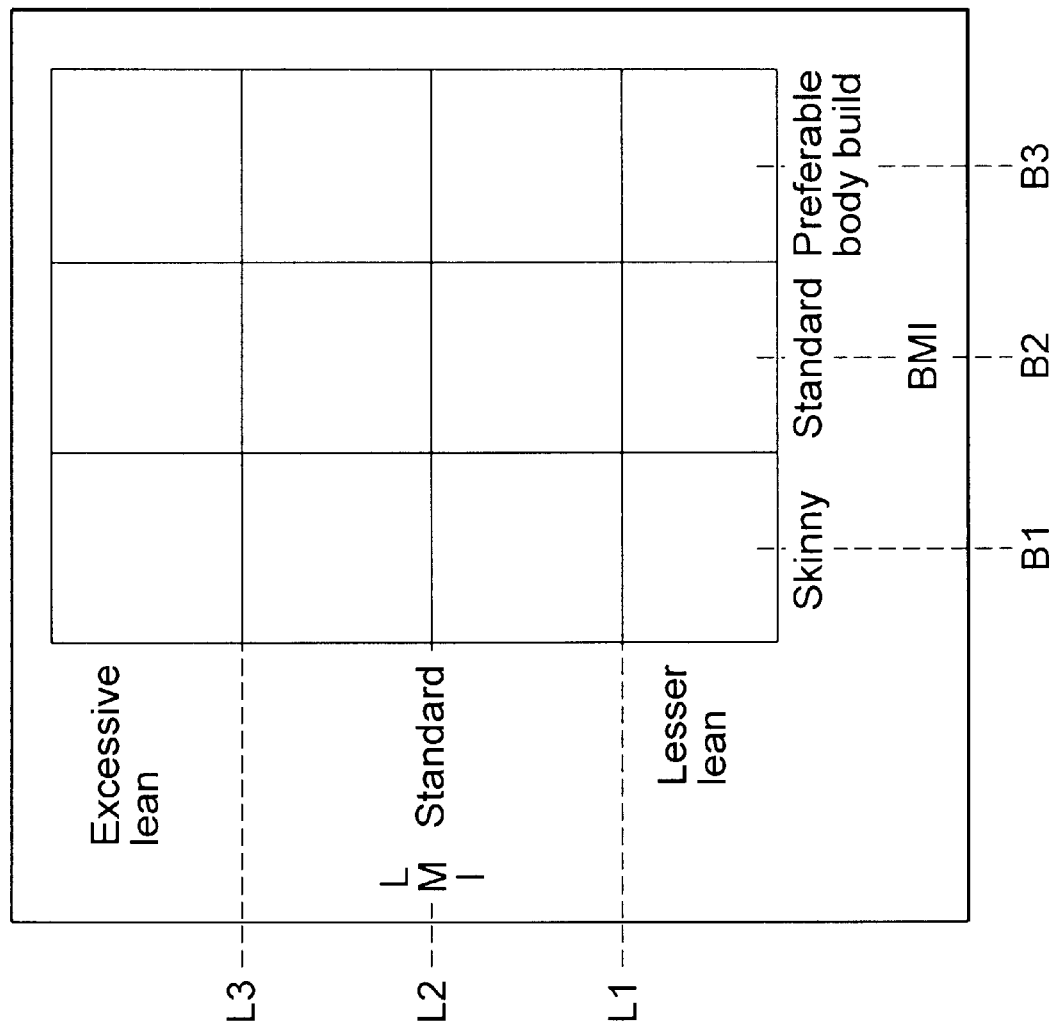
FIG. 9 is a chart illustrating a relationship between the BMI and the LMI.

In an actual display, the representation may be provided schematically in the form of matrix as illustrated in FIGS. 8 and 9. FIG. 8 is a graphic chart of the BMI and the FMI represented by way of the matrix. FIG. 9 is also a graphic chart of the BMI and LMI represented by way of the matrix.

In FIG. 8, the BMI is divided into three sections designated as follows:

B1 section for the values lower than 18.5;

B2 section for the values in a range of 18.5 to 25; and

B3 section for the values greater than 25.

Further, the FMI is divided into four sections designated as follows:

F1 line representing the FMI minimum acceptable values;

F2 line representing the FMI maximum acceptable values; and

F3 line representing the FMI obesity boundary values.

Also in FIG. 9, the BMI is divided into three sections similarly to FIG. 8. Further, the LMI is divided into four sections designated as follows:

L1 line representing the LMI obesity boundary values;

L2 line representing the LMI minimum acceptable values; and

L3 line representing the LMI maximum acceptable values.

It is to be noted that the criteria as described above may have been stored in the memory 44 beforehand.

Then, at step 8, the relationship between the calculated BMI and FMI and also the relationship between the calculated BMI and LMI are together at the same time indicated in the display device 42 in the form of graph of matrix as illustrated in FIGS. 8 and 9.

An example will now be described. It is to be appreciated that how the body fat rate is calculated from the bioelectric impedance has been taught in the aforementioned Japan Patent Application Laid-open No. H-10-192258, and the explanation thereof should be omitted herein.

<For a subject of a male aged 22, 170 cm high and weighed 75 kg with the body fat rate of 16%>

BMI: body weight/height$^2$=75/1.7$^2$=26,

Body fat mass: body fat rate×body weight/100=16×75/100=12,

FMI: body fat mass/height$^2$=12/1.7$^2$=4.15≈4.2, and

LMI: BMI−FMI=26−4.15=21.85≈21.9.

Therefore, the resultant BMI is 26, FMI 4.2 and LMI 21.9.

Figure 10:
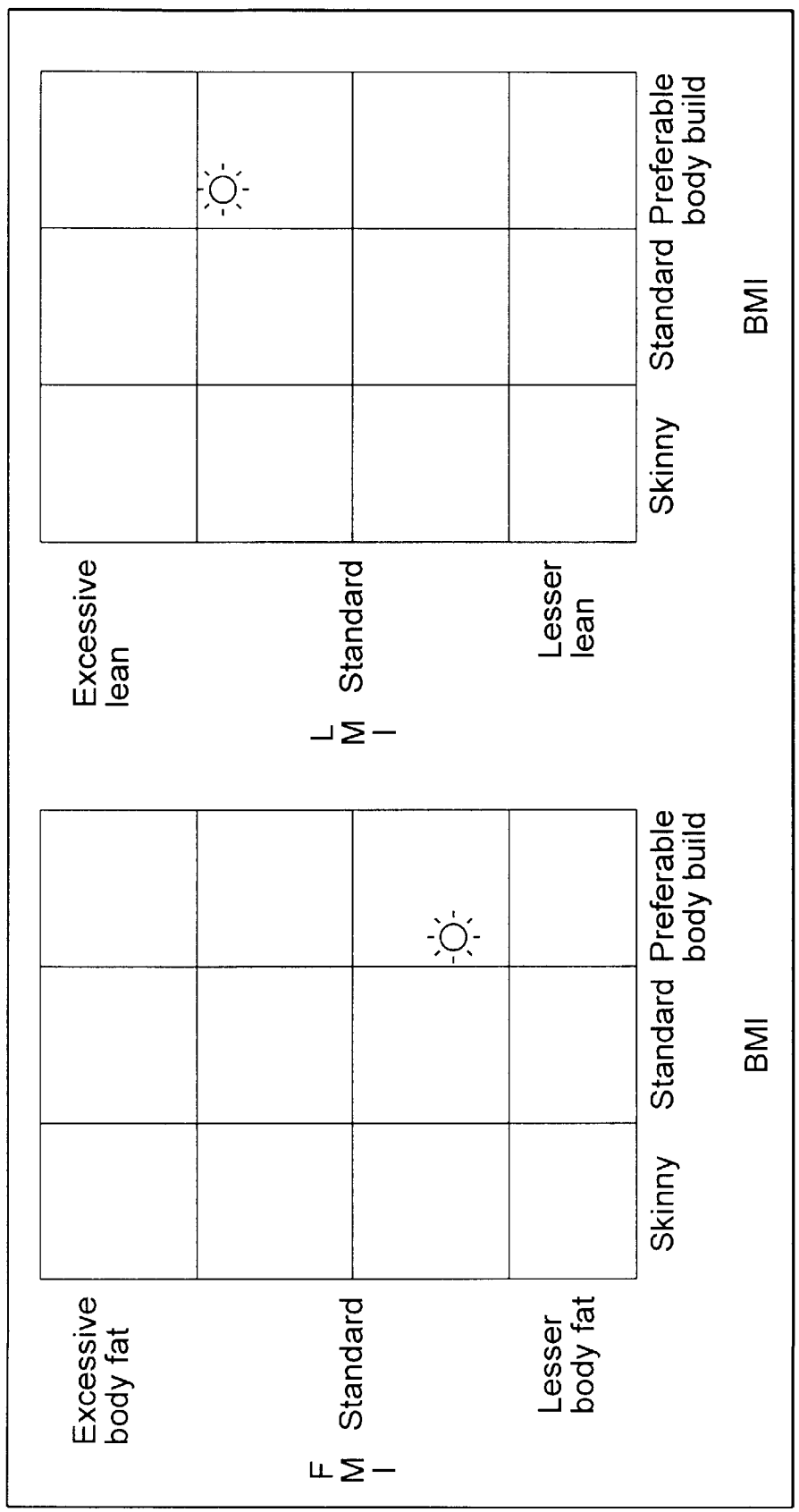
FIG. 10 is an example of indication in the body type determination apparatus of an embodiment according to the present invention.

FIG. 10 shows those values as a graphic representation. Observing the graphic representation, it can be seen from the graph of BMI−FMI that the ratio of fat tissue is held in the acceptable range, though the BMI is in the obese range. On the other hand, it can be seen from the graph of BMI−LMI that the ratio of the lean tissue is quite high. That is, the BMI at high level comes from the fact that the lean tissue such as muscles or bones occupying a large part of the body and such a body could be considered an athlete-type body rather than obesity.

At step 9, those values such as the BI and body weight measured at this time, the calculated BMI, FMI and LMI, and the like are stored in the memory 44. Thereafter, at step 10, the power is automatically turned off and the measurement procedure comes to the end.

A graphic representation mode starts at step 11. It is determined whether or not the graph key 41f is depressed, and if depressed, then the graphic representation for the last time measurement as shown in FIG. 10 is displayed at step 12.

Further, at step 13, it is determined whether or not the up key 41c and/or the down key 41d are depressed. At that time, if depressed, at step 14, the display is switched to show the representation shown in FIG. 11. At this point of time, if the up key 41c and/or the down key 41d are further depressed, the display returns to the graph shown in FIG. 10. In this way, at step 13, each time when the up key 41c and/or the down key 41d are depressed, the graphic representation is switched to another at step 14.

In the representation mode of FIG. 11, an ideal body constitution model and an actual body constitution of the subject are indicated. In this mode, there has been generated the healthy and ideal body constitution model that has not only the same sex and age but also the same body height as the subject so that the body weight, FMI and LMI of the ideal model may be compared with those for respective subjects.

By way of explanation of this indication mode, a case of the same subject as described above will be described in detail.

<For the subject being a male aged 22, 170 cm high and weighed 75 kg with body fat rate of 16%>

As described above, it has been known that the FMI=4.2 and the LMI=21.9.

By using the known data for the subject being under thirty and the ideal body type BMI=22, the acceptable FMI and the acceptable LMI can be derived from those graphs of FIGS. 8 and 9. For this person, the acceptable FMI is in a range of 3.1 to 4.4 and the acceptable LMI is in a range of 17.6 to 18.9.

The display mode uses 22 blocks for the representation of the standard body type since the BMI for the standard body type is 22, while 26 blocks is used for the representation of the subject since the BMI for the subject is 26. Since the body height is same as that of the subject, the height of the block building is corresponding to the height of the 22-block building and the exceeding blocks are separately built aside to facilitate the understandable representation.

Further, the FMI is represented by colored blocks and the LMI by non-colored blocks. That is, the colored is representative of the fat mass and the non-colored is representative of the lean mass. It can be found from the display of more blocks in spite of the same body height, the body weight of the subject is greater compared to the standard.

On the other hand, if the interest is directed only to the colored blocks representing the fat mass for comparison, it can be seen that the fat mass of the subject is within the standard range. Also, if the interest is directed only to the non-colored blocks representing the lean mass, it can be seen that the lean mass of the subject is more than the standard.

Taking all of the above factors into consideration, it is determined that the fat mass is within the standard range and therefore the heavier body weight is due to the more lean mass. Accordingly, it is visually understood from the comparison to the standard body type model having the same height that this subject is categorized as the person of the body constitution of athlete type having more lean mass such as muscles and bones. Thereby, it may be possible to simulate on the chart an ideal body type of the same age, sex and body height as of the individual subject so as to provide a visually understandable comparison of the FMI, LMI and BMI.

Further, the display may be provided in such a manner as shown in FIGS. 12A and 12B, in which an advisory message is given to the subject according to the determined body type. The tables of FIGS. 12A and 12B show a relationship between the indexes and the contents of the advisory messages for the male under thirty, which helps the subject to more deeply understand his constitution not only by the visual indication but also by words, thus facilitating the easy-understanding indication of his constitution.

At step 13, if neither of the up key 41c nor the down key 41d is depressed, it is determined at step 15 whether the power switch 41a is depressed or not. If the power switch 41a has been depressed, then the process goes to step 10 to turn off the power, while if not depressed, then the process returns to step 12 and continues to indicate the currently selected graphic representation.

Figure 13:
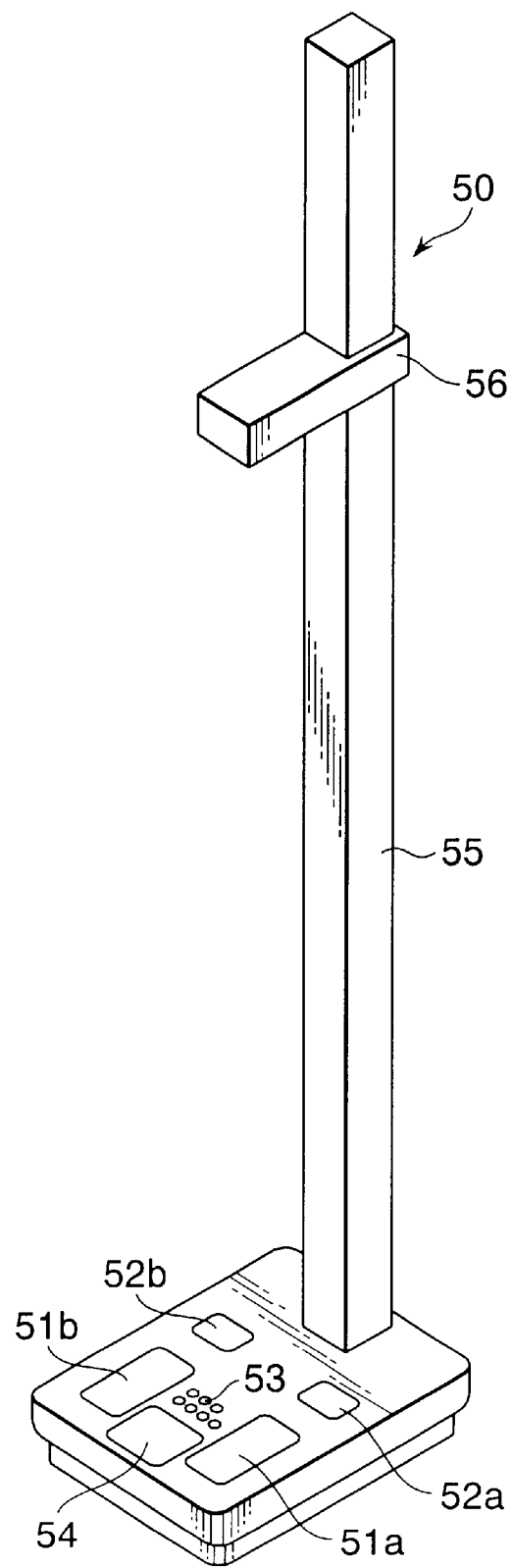
FIG. 13 is a schematic perspective view of a body type determination apparatus in conjunction with a body height meter according to an embodiment of the present invention.

A body type determination apparatus according to a second embodiment will now be described, in which the body height can be measured as well. FIG. 13 shows a body type determination apparatus equipped with a body height meter that can measure the body height of a subject as well as a bioelectric impedance and a body weight.

The body type determination apparatus 50 equipped with the body height meter comprises, on its loading face, current feeding electrodes 51a and 51b and voltage measuring electrodes 52a and 52b so as to measure the bioelectric impedance. Further, data input device 53 is used to enter a sex, age and so on. Measured results are indicated in a display device 54 by way of a graph, illustration or the like, as shown with respect to the first embodiment. In addition, the apparatus 50 has a pole 55 provided with a cursor 56 capable of moving along the pole 55.

It is to be appreciated that the operation procedure in this embodiment is the same as in the first embodiment, in which following to the measurements of the body weight and the bioelectric impedance, the cursor 56 is automatically made operative so as to measure the body height of the subject. The height measured herein is to be directly used upon calculating the BMI, the FMI and the LMI.

Thereby, the subject is only required to set beforehand his/her sex and age, while currently measured values are applied to all the other changeable values such as height, weight and bioelectric impedance, and thus the respective indexes can be calculated from the currently accurate values allowing a precise determination to be achieved.

Although the preferred embodiments of the present invention have been described in detail, the form of the indication is not limited to those, and for example, the number of divided segments included in the graphs of matrix shown in FIGS. 8 and 9 may be changed as desired.

Further, although in the above-described representation mode, the LMI has been indicated as an index of the lean tissue, the representation mode may be modified so that the LMI may be treated as an index of the muscular tissue since generally the lean tissue is mostly consisting of the muscular tissue. Thereby, providing an indication of whether the muscle mass being more or less rather than the indication of the lean tissue mass, which is unfamiliar word to the ordinary people, can help the subject understand the indication more easily.

Further, instead of the indication form using the block building as shown in FIG. 11, a human body figure may be employed, wherein the figure may have an enlarged outer contour for a higher BMI while it may have a reduced outer contour for a lower BMI, and further the color within the figure may be changed according to the ratio of the FMI to the LMI to indicate distinctively the ratio of the body fat to the muscle.

Still further, although in the above embodiments, the present invention has been described as the body type determination apparatus, in which the BMI, the FMI and the LMI have been calculated from the measured impedance and the results are provided in the form of graphic representation, the apparatus may be designed as a body type determination apparatus capable of measuring the body fat as well, in which the body type determination function according to the present invention is incorporated into a prior-art body fat meter in a built-in manner.

Yet further, although in the above embodiments, the body weight has been measured together with the bioelectric impedance at the same time, the apparatus may be designed such that the body weight may be entered by using an input device, and also the bioelectric impedance is not necessarily measured between the feet but can be measured between hands or between a hand and a foot.

Effect of the Invention

According to a body type determination apparatus of the present invention, which measures a bioelectiic impedance, calculates a BMI, a FMI and a LMI from entered body data, and provides a matrix representation or a indication by way of a simple geometry to facilitate an easy understanding of a relationship between the BMI and the FMI and/or a relationship between the BMI and the LMI, it may be possible to grasp the ratio of occupancy of fat tissue and lean tissue in the body constitution and to provide a comprehensive evaluation on the body type.

Since a subject can grasp the fat mass and the lean mass, undesirably excessive diet may be practiced on lesser occasions, and the risk of giving a hazard to health may be reduced.

Especially, the present invention allows the lean mass to be known and thus the muscle mass to be grasped, which is useful to grasp a basal metabolic amount, though not much attention has been paid until now, and thus the subject can see whether or not his/her body is a type of body that is apt to gain the body fat. Thereby, in the case of the body of the subject being categorized as the type that is more likely to gain the body fat, the subject may try to be more careful in his/her daily life in advance and thus to prevent the obesity.

What is claimed is:

1. A body type determination apparatus comprising an input device, an impedance measuring device, an arithmetic device and a display device, wherein
said input device enters personal body data;
said impedance measuring device measures a bioelectric impedance;
said arithmetic device calculates an FMI and a BMI based on said entered personal body data and measured bioelectrical impedance value; and
said display device provides a graphic representation of a relationship between the calculated FMI and BMI.

2. A body type determination apparatus comprising an input device, an impedance measuring device, an arithmetic device, and a display device, wherein
said input device enters personal body data;
said impedance measuring device measures a bioelectrical impedance;
said arithmetic device calculates an LMI and a BMI based on said entered personal body data and measured bioelectrical impedance value; and
the display device provides a graphic representation of a relationship between the calculated LMI and BMI.

3. A body type determination apparatus comprising an input device, an impedance measuring device, an arithmetic device and a display device, wherein
said input device enters personal body data;
said impedance measuring device measures a bioelectrical impedance;
an arithmetic device calculates an FMI, an LMI and a BMI based on said entered personal body data and measured bioelectrical impedance value; and
a display device provides a graphic representation of both a relationship between the calculated FMI and BMI and a relationship between the calculated LMI and BMI, all at once.

4. A body type determination apparatus in accordance with claim 1 or 3, in which said graph to be indicated in said display device is a representation in matrix of a relationship between the FMI and the BMI.

5. A body type determination apparatus in accordance with claim 2 or 3, in which said graph to be indicated in said display device is a representation in matrix of a relationship between the LMI and the BMI.

6. A body type determination apparatus comprising an input device, an impedance measuring device, an arithmetic device and a display device, wherein
said input device enters personal body data;
said impedance measuring device measures a bioelectric impedance;
said arithmetic device calculates an FMI, an LMI and a BMI based on said entered body data and measured bioelectric impedance value; and
said display device provides a representation of the calculated BMI by using blocks, said blocks being indicated distinctively in different colors based on the calculated FMI and LMI.

7. A body type determination apparatus in accordance with claim 6, in which said arithmetic unit calculates ideal FMI and LMI for an ideal model having the same sex, age and body height as of the personal body data entered from said input unit, and said display unit provides a representation of an ideal BMI by using blocks, wherein said representation by blocks is indicated in different colors each corresponding to said calculated ideal FMI and LMI.

8. A body type determination apparatus in accordance with any one of claim 1, 2, 3, 6 or 7, further comprising a body weight measuring device, wherein said body weight measuring device measures a body weight, and said arithmetic device uses the measured body weight value to calculate the BMI.

9. A body type determination apparatus in accordance with any one of claim 1, 3, 6 or 7, further comprising a body height measuring device,
wherein said body height measuring device measures body height, and said arithmetic device uses the measured body height to calculated the FMI and the BMI.

10. A body type determination apparatus in accordance with any one of claim 2, 3, 6 or 7, further comprising a body height measuring device,
wherein said body height measuring device measures body height, and said arithmetic device uses the measured body height to calculate the LMI and the BMI.

* * * * *